United States Patent
Bertagna

(10) Patent No.: US 11,031,110 B2
(45) Date of Patent: Jun. 8, 2021

(54) SYSTEM AND METHOD FOR PROCESSING LOCATION DATA

(71) Applicant: Inpixon, Palo Alto, CA (US)

(72) Inventor: Patrick E. Bertagna, Los Angeles, CA (US)

(73) Assignee: Inpixon, Palo Alto, CA (US)

(*) Notice: Subject to any disclaimer, the term of this patent is extended or adjusted under 35 U.S.C. 154(b) by 514 days.

(21) Appl. No.: 15/886,895

(22) Filed: Feb. 2, 2018

(65) Prior Publication Data
US 2018/0293254 A1 Oct. 11, 2018

Related U.S. Application Data

(63) Continuation of application No. 12/378,153, filed on Feb. 11, 2009, now Pat. No. 9,910,862.

(51) Int. Cl.
| | |
|---|---|
| *G16H 10/60* | (2018.01) |
| *G06F 16/29* | (2019.01) |
| *G16H 40/67* | (2018.01) |
| *G06F 19/00* | (2018.01) |

(52) U.S. Cl.
CPC ............ *G16H 10/60* (2018.01); *G06F 16/29* (2019.01); *G06F 19/00* (2013.01); *G16H 40/67* (2018.01)

(58) Field of Classification Search
CPC ......... G06F 16/29; G06F 19/00; G16H 10/60; G06Q 50/24; G06Q 50/22
See application file for complete search history.

(56) References Cited

U.S. PATENT DOCUMENTS

| | | | | |
|---|---|---|---|---|
| 6,243,039 | B1* | 6/2001 | Elliot | G01S 19/16 342/357.74 |
| 7,214,065 | B2* | 5/2007 | Fitzsimmons, Jr. | G09B 5/00 434/236 |
| 7,509,215 | B2* | 3/2009 | Shen | G01C 21/00 340/995.24 |
| 2002/0120397 | A1* | 8/2002 | Kepler | G01C 21/3644 701/426 |

* cited by examiner

*Primary Examiner* — Linh Giang Le
(74) *Attorney, Agent, or Firm* — Pillsbury Winthrop Shaw Pittman, LLP; Joshua L. Tucker

(57) ABSTRACT

A novel system and method for processing location data are disclosed. An exemplary method includes receiving location data from a remote device, associating the location data with a particular subscriber, augmenting the location data in one of a plurality of predetermined ways based on information associated with the particular subscriber to produce augmented location data, and providing the augmented location data to the subscriber. In a more particular embodiment, the step of augmenting the location data includes retrieving a subscriber file associated with the subscriber and performing one or more augmentation processes on the location data based at least in part on the subscriber file. An example system includes both a remote device operative to transmit location data and a central station for performing the methods of the present invention.

21 Claims, 6 Drawing Sheets

SYSTEM AND METHOD FOR PROCESSING LOCATION DATA

RELATED APPLICATIONS

This application is a continuation of U.S. patent application Ser. No. 12/378,153, filed Feb. 11, 2009 by the same inventor, which is incorporated herein by reference in its entirety.

BACKGROUND OF THE INVENTION

Field of the Invention

This invention relates generally to a system and method for processing location data, and more specifically to a system and method for processing location data based on one or more different location data augmentation routines selected by a user.

Description of the Background Art

Currently, systems exist for tracking the location of persons and/or property. Generally, such systems include a mobile tracking device carried by the person and/or the property being monitored. The mobile tracking device transmits location data to a central station.

Such mobile tracking devices typically include a GPS receiver and a wireless cellular modem. The GPS receiver picks up satellite signals indicative of the user's global position. The cellular modem then sends the position data (e.g., longitude and latitude coordinates) to a central station where it undergoes augmentation. In particular, the longitude and latitude coordinates are augmented so as to be displayed on a street map or the like. The central station typically includes a server connected to the internet so that a subscriber can log on to the server with another computer connected to the internet and monitor the mobile tracking device in real-time.

Although advances in tracking system technology have been made over the past several years, technology for providing users access to the tracking data (e.g., internet tracking) is still relatively unexplored. One shortcoming in current technology is that users are limited to whatever particular augmentation service the central station provides. Therefore, if a user prefers multiple specific augmentation services the user will have to log on to one server for a specific augmentation and then log on to another server for another specific augmentation, assuming the desired augmentations are even available.

What is needed, therefore, is a tracking system and method that can augment tracking data in multiple ways and provide the augmented tracking data to a user. What is also needed is a tracking system and method that can augment tracking data based on information and preferences provided by a particular user and then provide the augmented data to that user. What is also needed is a tracking system and method that stores augmentation preferences for a plurality of users.

SUMMARY

The present invention overcomes the problems associated with the prior art by providing a system and method for processing and providing location data. The method of providing location data includes receiving location data from a remote device, associating the location data with a particular subscriber, augmenting the location data in one of a plurality of predetermined ways based on information associated with the particular subscriber to produce augmented location data, and providing the augmented location data to the subscriber. More particularly, the step of augmenting the location data includes retrieving a subscriber file associated with the subscriber and performing one or more augmentation processes on the location data based at least in part on the subscriber file associated with the subscriber.

According to one particular method, the step of augmenting the location data includes using the location data to retrieve additional information from one or more remote sources and using the additional information to augment the location data. The remote source(s) can include one or more discrete public databases, one or more discrete private databases, or a combination of discrete public and private databases.

According to another particular method, the step of augmenting the location data includes performing at least one of a plurality of predetermined processes on the location data. For example, one predetermined process includes comparing the location data to data previously provided by the subscriber. Another predetermined process determines the proximity of the tracking device to a position associated with the data previously provided by the subscriber. Yet another predetermined process includes comparing the location data to location data retrieved from a remote data source.

The methods of the present invention can also be embodied in code in a non-transitory, computer readable medium, where the code causes one or more electronic devices to perform the method(s) defined by the code. The term "non-transitory" is intended to distinguish storage media from transitory electrical signals. However, rewritable memories are considered to be "non-transitory".

A system for monitoring a tracking device is also disclosed. That system includes both a remote device operative to transmit location data and a central station. The central station includes an input device operative to receive the location data, a data augmenter operative to augment the location data in one of a plurality of predetermined ways based on information associated with a particular subscriber to produce augmented location data, and an output device operative to provide the augmented location data to the subscriber. In a particular embodiment, the data augmenter retrieves a subscriber file associated with the subscriber and performs one or more augmentation processes on the location data based at least in part on the subscriber file associated with the subscriber.

The data augmenter can also use the location data to retrieve additional information from a remote source and use the additional information to augment the location data. The remote source can include one or more discrete public databases and/or one or more discrete private databases.

According to another embodiment, the system of the present invention can include both a remote device operative to transmit location data and a central station where the central station includes an input device operative to receive the location data, means for augmenting the location data in one of a plurality of predetermined ways based on information associated with a particular user to produce augmented location data, and an output device operative to provide the augmented location data to the user.

BRIEF DESCRIPTION OF THE DRAWINGS

The present invention is described with reference to the following drawings, wherein like reference numbers denote substantially similar elements.

DETAILED DESCRIPTION

The present invention overcomes the problems associated with the prior art by providing a system and method for augmenting location data that can be customized to the preferences of each individual subscriber. In the following description, numerous specific details are set forth (e.g., particular augmentation routines, particular data flow diagrams, etc.) in order to provide a thorough understanding of the invention. Those skilled in the art will recognize, however, that the invention may be practiced apart from these specific details. In other instances, details of well known global positioning system components and network communications protocols have been omitted, so as not to unnecessarily obscure the present invention.

Figure 1:
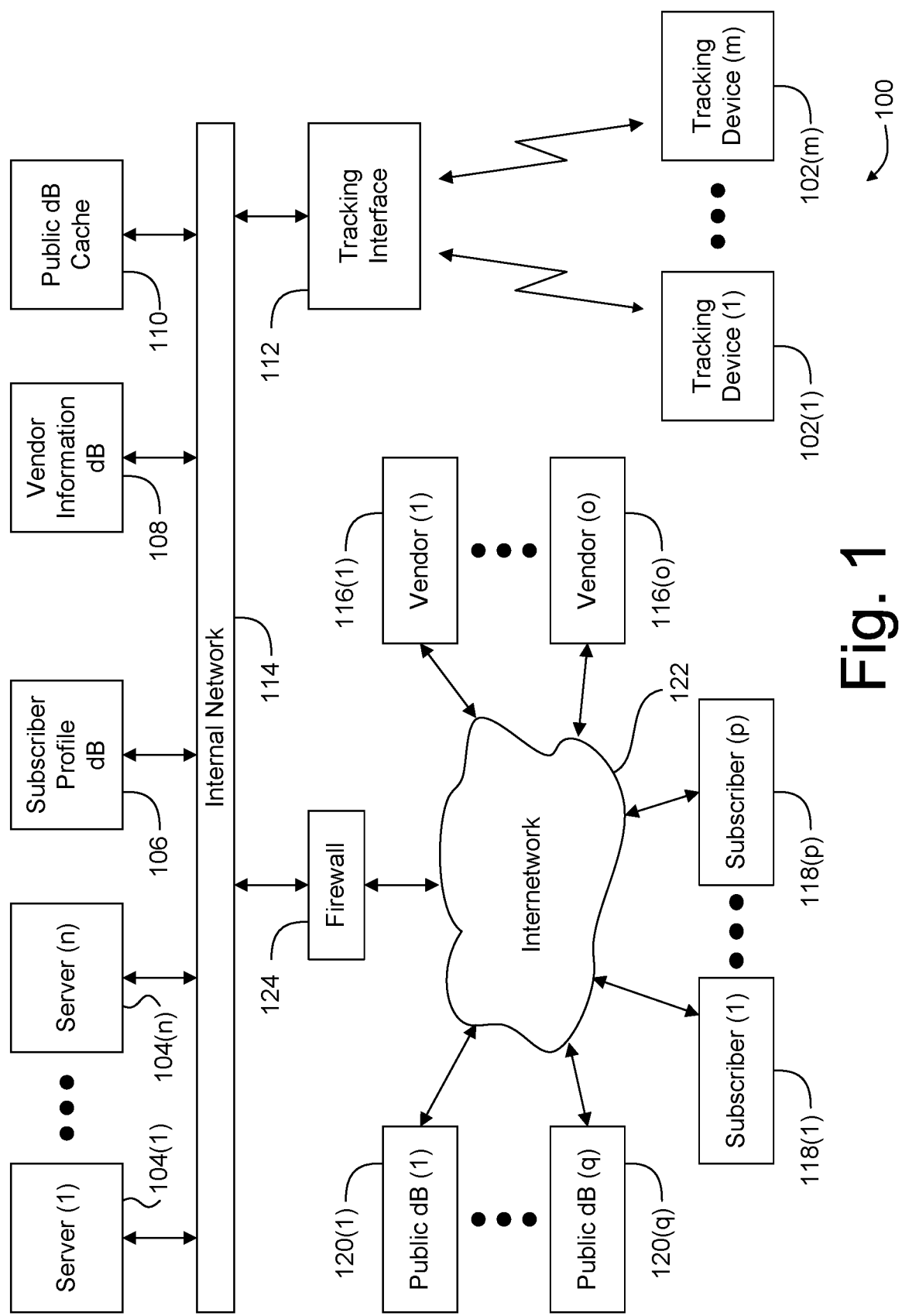
FIG. 1 is a block diagram of a system for tracking one or more tracking devices and providing augmented tracking information to subscribers according to the present invention.

FIG. 1 is a block diagram of a system 100 for tracking and/or monitoring one or more tracking devices 102(1-*m*) and for providing customized augmented location data to each of a plurality of subscribers associated with the tracking devices 102(1-*m*). System 100 includes a plurality of tracking devices 102(1-*m*), one or more servers 104(1-*n*), a subscriber profile database 106, a vendor information database 108, a public database cache 110, and a tracking interface 112, all intercommunicating via an internal network 114. System 100 also includes one or more vendors systems 116(1-*o*), one or more subscribers systems 118(1-*p*), and one or more public databases 120(1-*q*), which all communicate with an internetwork 122 (e.g., the Internet). Internal network 114 is also connected to internetwork 122 through a firewall 124, which provides a measure of security for internal network 114 against incoming threats from internetwork 122.

In the present embodiment, subscriber profile database 106, vendor information database 108, public database cache 110, vendors 116(1-*o*), subscribers 118(1-*p*), and public databases 120(1-*q*) are all remote data sources that provide information to servers 104(1-*n*). Subscriber profile database 106, vendor information database 108, and public database cache 110 are all private remote data sources because they are connected to internal network 114. In contrast, vendor systems 116(1-*o*), subscriber systems 118 (1-*p*), and public databases 120(1-*q*) are all public data sources because they communicate with servers 104(1-*n*) via internetwork 122. Note that the private remote data sources and the public remote data sources are discrete elements. So, subscriber profile database 106 is not necessarily embodied in the same electronic device as vendor information database 108 or public database cache 110. Similarly, public database 120(1) can be a separate database from public database 120(*q*).

The elements of tracking system 100 provide the following general functions. Tracking devices 102(1-*m*) provide geographical location data (e.g., latitude and longitude coordinates, etc.) indicating their geographical locations to servers 104(1-*n*) via tracking interface 112. Servers 104(1-*n*) perform tracking services for subscribers using subscriber systems 118(1-*p*) and augment location data received from tracking devices 102(1-*m*) so that the subscribers using subscriber systems 118 (1-*p*) can track and/or monitor their associated tracking device(s) 102(1-*m*) in a customized, augmented manner. Subscriber profile database 106 stores information, including customized augmentation preferences, associated with each subscriber. Vendor information database 108 stores information about vendors using vendor systems 116(1-*o*), such as the vendor's name, address, and phone number, and optionally, information about goods and services offered by the vendor. Public database cache 110 provides storage for data retrieved from public databases 120(1-*q*), or optionally, another remote public data source. Servers 104(1-*n*) use the temporary data stored in public database cache 110 to augment location data for subscribers using subscriber systems 118(1-*p*). Tracking interface 112 receives data and commands from servers 104(1-*n*) (e.g., location request signals, control routines, etc.) and transmits the data and commands to the destination tracking devices 102(1-*m*). Tracking interface 112 also receives data (e.g., location data, sensor readings, alert signals, etc.) from tracking devices 102(1-*m*) and provides the received data to one or more servers 104(1-*n*). In the present embodiment, tracking interface 112 interfaces with tracking devices 102 (1-*m*) wirelessly, such as via a cellular network. Vendor systems 116(1-*o*) are used by vendor-businesses, whose information can be included in augmented location data. Optionally, the vendors can use vendor systems 116(1-*o*) to communicate with and update information stored about them in vendor information database 108 directly via internetwork 122. Public databases 120(1-*q*) provide information to servers 104(1-*n*) that is used to augment location data for subscriber systems 118(1-*p*). Public databases 120(1-*q*) include any publicly accessible database, such as a telephone directory, a sex offender registry, etc.

Subscribers systems 118(1-*p*) are electronic devices that allow a human subscriber/user to electronically interact with servers 104(1-*n*) to define data augmentation preferences and to obtain customized augmented location data and alerts from their associated tracking device(s) 102. For instance, when a user initially subscribes to the tracking system 100, the subscriber optionally sets up a username and password with one of servers 104 via a subscriber system 118. That server 104 would also create a subscriber profile uniquely associated with that subscriber and then allow the subscriber (again via subscriber system 118) to customize what augmentation routines the subscriber would like to augment the location data received from his tracking device 102 with. Server 104 then stores the subscriber's profile in subscriber database 106. In addition, if a subscriber registers more than one tracking device 102 with system 100, then a separate subscriber profile can be created in subscriber profile database 106 for each tracking device 102 associated with the subscriber. Alternatively, multiple tracking devices 102 can be associated with a single subscriber profile in database 106, for example, where the subscriber wishes to run the same augmentation routines on the location data provided by each associated tracking device 102. The subscriber profiles in database 106 also contain any other pertinent information associated with a subscriber such as personal information (address, telephone number, etc.), payment information such as a credit card number, a network identifier uniquely identifying the subscriber 118 on the network 122, etc.

Generally, a server 104 operates as follows to provide customized augmented location data to a subscriber using a subscriber system 118. Server 104, upon receiving the location data from a tracking device 102, associates the location data with a particular subscriber, augments the location according to one or more of a plurality of predetermined routines based on information associated with the subscriber, and then presents the augmented location data to the subscriber via internetwork 122 and an associated subscriber system 118. Note that the predetermined augmentation routines could be defined in the subscriber's profile stored in subscriber profile database 106, or could have been input manually by the subscriber via subscriber system 118 before the location data was augmented as will be described below. Examples of particular augmentation routines that server 104 can carry out also will be discussed below.

It should be noted that the present embodiment is described with respect to "subscribers" using subscriber systems 118, implying that the subscribers pay for the services provided by tracking system 100. For example, subscription services offered for a subscriber's use of system 100 could vary by price based on any number of criteria such as the complexity of the augmented location data provided, the number of augmentation routines employed by the subscriber, the augmented location data delivery method, the number of tracking devices 102 associated with a subscriber, and so on. However, tracking system 100 is not limited to a subscription type business model. For example, access to system 100 could be provided to the subscribers for free, and system 100 could rely on some other business model to raise revenue.

Figure 2:
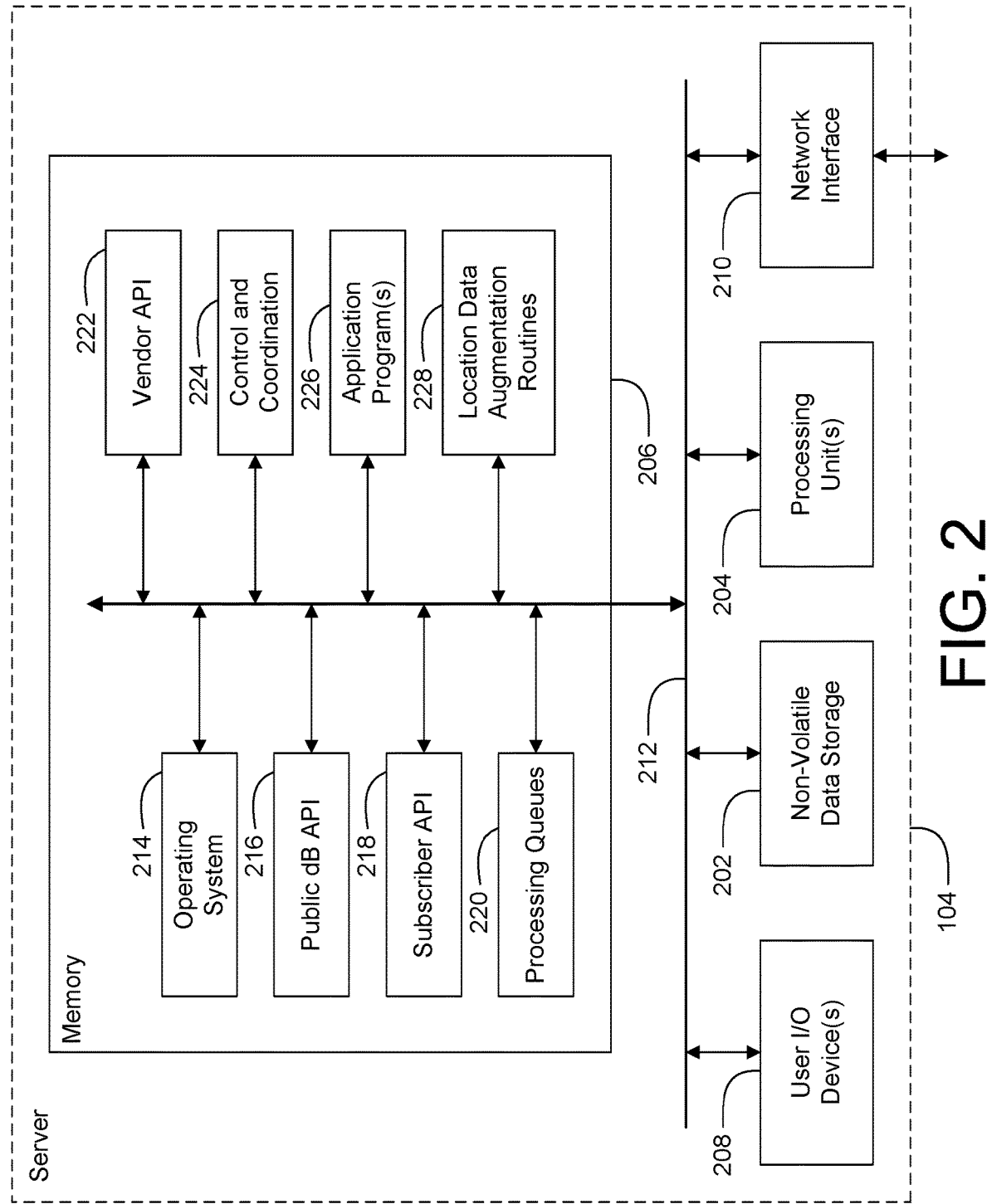
FIG. 2 is a block diagram of a server of the tracking system of FIG. 1.

FIG. 2 is a block diagram showing one of servers 104(1-n) of tracking system 100 in greater detail. Server 104 acts as a central station for tracking system 100 and causes data to be augmented according to the present invention. Each server 104 includes non-volatile data storage 202, one or more processing units 204, working memory 206, one or more user I/O device(s) 208, and a network interface 210. Nonvolatile data storage 202 (e.g., hard disk drives, optical disk drives, etc.) stores data and code that is retained therein even when server 104 is powered down. Working memory 206 stores data and code that, when processed by processing unit(s) 204, imparts functionality to server 104. User input/output devices 208 (e.g., keyboard, mouse, monitor, etc.) provide a means of interaction between server 104 and a local user, such as a server administrator. Network interface 210 provides a communication link to internal network 114 such that server 104 can communicate with other devices connected to internal network 114 and internetwork 122. For example, network interface 210 enables server 104 to communicate with tracking interface 112 via internal network 114 so that server 104 can communicate with tracking devices 102(1-m). Network interface 210 acts as an input device that permits server 104 to receive location data from tracking devices 102(1-m) and as an output device that permits server 104 to transmit augmented location data to a subscriber system 118.

Working memory 206 includes an operating system 214, a public database API 216, a subscriber API 218, one or more processing queues 220, a vendor API 222, control and coordination routines 224, one or more application program(s) 226, and a plurality of location data augmentation routines 228. Data and code are shown in working memory 206 as functional blocks for the sake of clear explanation. It should be understood, however, that the various functions of server 104 need not be run in any particular location of working memory 206 and may be grouped in any useful manner. For example, the several application program interfaces (APIs) shown could be grouped into a single API. It should also be noted that the modules in working memory 206 are loaded into working memory 206 when server 104 is powered up, such as from non-volatile data storage 202.

The modules of working memory 206 are means for augmenting location data and provide the following functions. Operating system 214 provides low level control of server 104 and provides a platform on top of which the other modules and programs can operate. Public database API 216 provides a means for server 104 and public databases 120(1-q) to communicate with one another. Subscriber API 218 provides a means for server 104 and subscriber systems 118(1-p) to communicate with one another. Processing queues 220 provide temporary storage for various processing requests on server 104, such as location data that is awaiting augmentation, connections with subscriber systems 118(1-p), location request transmissions to tracking devices 102, etc. Vendor API 222 provides a means for servers 104 and each of vendor systems 116(1-o) to communicate with one another. Control and coordination module 224 provides overall control and coordination of the tracking, monitoring, augmentation, and subscriber services provided by server 104. For example, control and coordination module 224 processes location and/or sensor data received from tracking devices 102, augments the location and/or sensor data using one or more of the location data augmentation routines 228 based on information associated with a particular subscriber, and provides the augmented location data to an associated subscriber system 118. In this manner, control and coordination module 224 serves as a location data augmenter. Control and coordination module 224 also contains programs that otherwise communicates with a subscriber system 118, read and/or update subscriber profile database 106, search remote data sources, such as public databases 120(1-q), update vendor information database 108, and so on. Application programs 226 represent other miscellaneous applications (e.g., security applications, database maintenance applications, etc.) running in working memory 206. Finally, server 104 employs location data augmentation routines 228 to augment location data for each of subscriber systems 118(1-p) in accordance with a subscriber's preferences.

Control and coordination module 224 employs one or more augmentation routines 228 when server 104 augments location data for a particular subscriber using a subscriber system 118. The executed augmentation routine(s) can be selected automatically based on the subscriber' profile in database 106 or can be selected in real time by the subscriber as he interacts with subscriber system 118 (e.g., via an internet web site running on subscriber system 118 that is hosted by server 104, etc.). The subscriber profiles in database 106 provide the advantage that server 104 can automatically employ the augmentation routines 228 specified in the subscriber's profile when the subscriber logs onto server 104 with a subscriber system 118 and makes a location request.

The specific augmentation routines 228 themselves are very versatile and can be easily customized to different subscribers' desires. For example, a subscriber may choose an augmentation routine 228 that displays the location of an associated tracking device 102 on a street map or, even more specifically, on a street map in relation to a particular street address input by the subscriber via a subscriber system 118. As another example, the subscriber may choose an augmentation routine 228 that displays the location of an associated tracking device 102 in relation to the address of the nearest building to the tracking device 102. Such an augmentation routine 228 could also present a phone number to the corresponding nearest building based on information retrieved from a telephone directory public database 120. In still another embodiment, the subscriber 118 may choose to augment location data with addresses of registered sex offenders within a particular geographical radius from the geographical location of the associated tracking device 102. As still another example, an augmentation routine 228 can use location data to present a subscriber (via subscriber system 118) with the speed and direction that an associated tracking device 102 is moving in. Indeed, location data augmentation routines 228 can run specific augmentations based on information received from one or more of subscriber profile database 106, vendor information database 108, public database cache 110, public databases 120(1-$q$), vendor systems 116(1-$o$), location data from tracking devices 102, or other input from subscribers 118(1-$p$).

The present invention advantageously provides a platform that is customizable for each individual subscriber based on his or her individual needs. Indeed, a subscriber can choose from a list of predefined augmentation routines 228 stored in a server 104. Alternatively, a customized augmentation routine 228 could be created for a subscriber based on their desires. For example, a subscriber using system 100 for personal reasons will likely find certain augmentation routines 228 more important (e.g., locations of registered sex offenders, etc.), while businesses will likely find other augmentations routines 228 more important (e.g., speed, direction or travel, estimated time of arrivals (ETA's) of their fleet vehicles, etc.). What is important to note, however, is that a subscriber can select from predefined augmentation routines 228 or define his own augmentation routines 228 to meet his individual needs. Even more particularly, predefined augmentation routines 228 can also be personalized for individual subscribers as well.

A commercial delivery company provides a useful example to illustrate the customizability of the present invention for a business. A commercial delivery company could create a custom subscriber profile in database 106 that employs several augmentation routines 228 to monitor the location of its trucks (each of which includes a tracking device 102) on their delivery routes. For example, the delivery company could enable predefined augmentations routines 228 that monitor the speed and direction of its trucks but disable irrelevant augmentation routines 228 such as a truck's proximity to registered sex offenders. In addition, the truck delivery company could request that a customized augmentation routine 228 be created and employed that utilizes the speed and direction augmented data to extrapolate an estimated time of arrival (ETA) of one of its delivery trucks based on a street address input by the delivery company via a subscriber system 118. In this manner, the delivery company utilizes predefined augmentation routines 228, as well as, created a custom augmentation routine 228 of its own to efficiently track its vehicle fleet.

As another example, a father could customize a predefined "geofence" augmentation routine 228 to monitor his child. According to the geofence augmentation routine, server 104 notifies the subscriber via subscriber system 118 when the tracking device 102 associated with the subscriber crosses a defined geographical boundary. In this example, if the father wanted to limit his child's movement to one block surrounding their house, then the father would define the one-block geographical boundary limits within his subscriber profile in database 106. The geofence augmentation routine 228 would then compare the geographical location of the tracking device 102 with the customized geofence boundaries in the father's subscriber profile, and alert the father via his subscriber system 118 if the location of his child's tracking device 102 broke the geofence boundary. In addition to the above example, information associated with the vendors using vendor systems 116(1-$o$) can also be used to define geofences, such as by type of business. For example, the same father described above could be notified if his child goes near an adult book store or a tavern. Similarly, public databases 120(1-$q$) can also provide information (e.g., sex offender registries, etc.) that can be used as criteria for defining geofences, such as the father could be notified if his child's location was near a sex offender's residence.

Augmentation routines 228 can also include routines that augment location data with vendor information from vendor information database 108. Such vendor information may be beneficial to a parent who is trying to assist a stranded child who is wearing a tracking device 102. For example, if a teenager's car breaks down, a parent may want to augment position data associated with the teenager's position with addresses and/or phone numbers of service stations near where the teenager is broken down. Alternatively, the teenager could receive such augmented position data herself if she had the necessary equipment (e.g., a cell phone) to communicate with servers 104(1-$n$). Vendor information database 108 can also store information regarding other commercial establishments, such as restaurants, service stations, police stations, hospitals, etc.

Vendor API 222 facilitates bi-directional communication between server 104 and vendor systems 116(1-$o$) via internetwork 122. Vendor API 222 enables servers 104 to exchange information with vendor systems 116, and for the same vendors to update their information stored in vendor information database 108. For example, control and coordination module 224 might solicit information from vendor systems 116(1-$o$) to update the information in vendor information database 108. Alternatively, a vendor using a vendor system 116 may want to communicate with control and coordination module 224 of a server 104 to update its information (e.g., address, phone number, etc.) stored in vendor information database 108. As another example, vendor API 222 enables control and coordination module 224 to communicate with a vendor system 116(1-$o$), such as to send the vendor an invoice for the services provided by server 104 (e.g., when server 104 provides information regarding the vendor to subscribers via augmented location data, etc.). In the present embodiment, control and coordination module 224 interacts with vendor systems 116(1-$o$) via vendor API 222 and updates vendor information database 108 on the vendors' behalves. However, vendor systems 116(1-$o$) could interact with vendor information database 108 via other means, such as a separate server dedicated to maintaining vendor information database 108.

Servers 104(1-$n$) also need to augment location data with information obtained from one or more public databases 120(1-$q$) in particular cases. Accordingly, public database API 216 enables a server 104 to communicate with any one of public databases 120(1-$q$). For example, public database API 216 could enable control and coordination module 224 to retrieve telephone number(s) from a public telephone database 120. As another example, public database API 216 could also enable control and coordination module 224 to communicate with a sex offender registry database 120. In any case, public database API 216 facilitates bidirectional communication between the modules of servers 104(1-n) and public databases 120(1-q). Control and coordination module 224 is also further operative to store information retrieved from public databases 120(1-q) via public database API 216 in public database cache 110 for concurrent or future use.

If should also be noted that augmentation routines 228 are not limited to augmenting location data. Augmentation routines 228 can also augment other types of sensor data received from one of tracking devices 102(1-m). For example, if a tracking device included a temperature sensor to be worn against the body, then an augmentation routine 228 could be operative to receive the temperature data and augment the temperature data to indicate if the tracking device 102 is not being worn properly or was removed (such as by a child). As another example, an augmentation routine 228 could receive input from a motion sensor and determine if the tracking device 102 was physically moving at the time the motion sensor data was produced. Similarly, a battery sensor in tracking device 102 could provide the charge state of the battery, and an augmentation routine 228 could augment the battery data (e.g., with a graphic, etc.) to indicate to the subscriber that the battery in the tracking device 102 needs changing. As still another example, control and coordination module could augment location data with sensor data.

Furthermore, as alluded to above, servers 104 can also provide alerts to subscriber systems 118(1-p). For example, if a tracking device 102 is cold or has not moved in a long time, control and coordination module 224 could augment the location/sensor data provided to subscriber system 118 with an alert indicating that the tracking device 102 is stationary. As another example, control and coordination module 224 could augment battery sensor data with an alert that the battery is depleted prior to sending the augmented sensor data to the subscriber system 118. As yet another example, a tracking device 102 could be provided with a panic alarm, and control and coordination module 224 could employ an augmentation routine 228 that augments location data with a panic alert signal. As still another example, control and coordination module 224 could employ an augmentation routine 228 that alerts the subscriber system 118 if the tracking device 102 breaks a geofence boundary. Note that control and coordination module 224 can be operative to automatically run such augmentation routines 228 designed to alert the subscriber system 118 as necessary, or it could only run alert augmentation routines 228 enabled by the subscriber (e.g., in a subscriber profile). Furthermore, it should be noted that such alerts could also be provided to server 104 directly from tracking devices 102, and server 104 could, in turn, provide the alerts to the associated subscriber systems 118.

Figure 3:
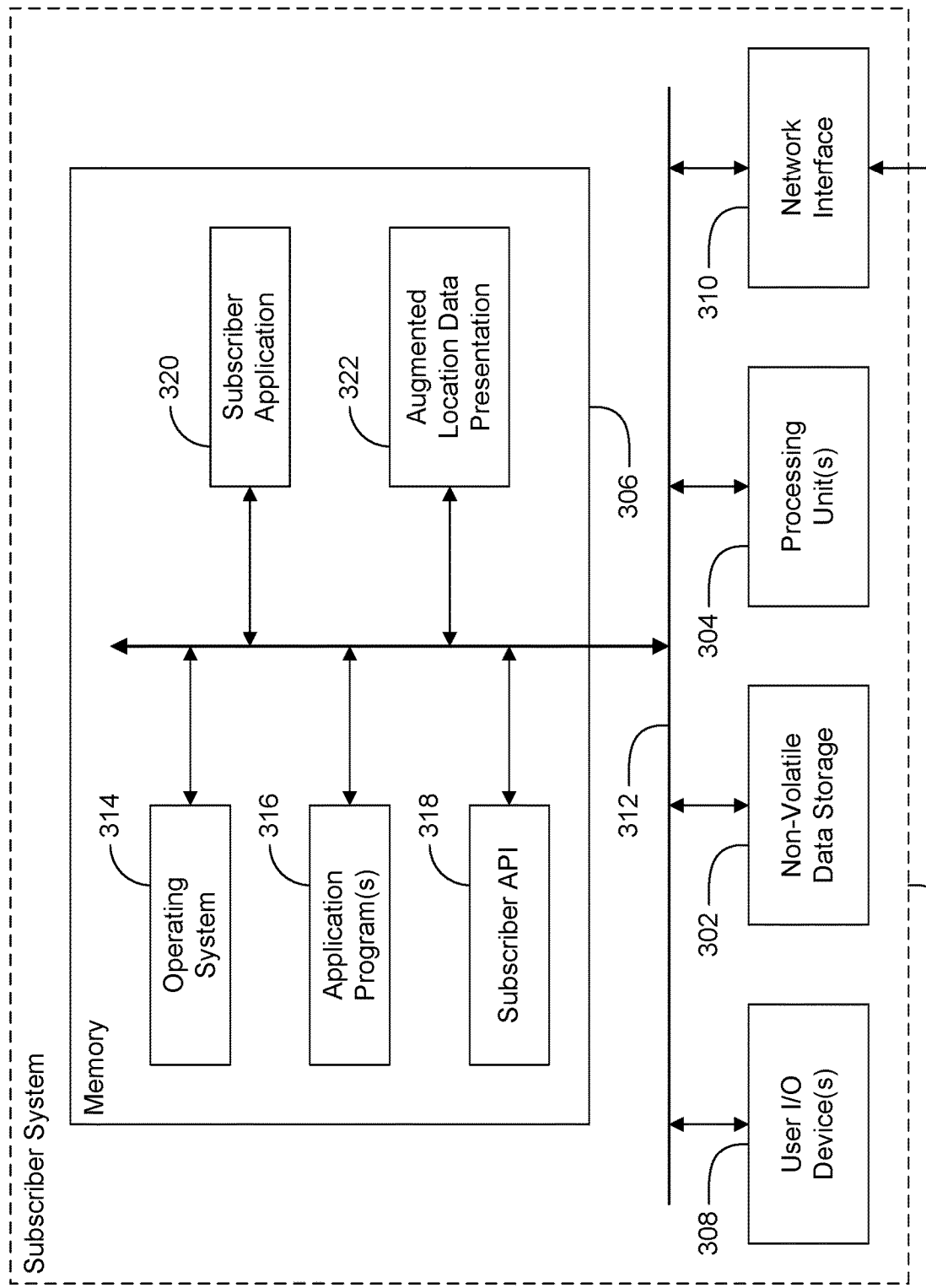
FIG. 3 is a block diagram of a subscriber system of the tracking system of FIG. 1.

FIG. 3 is a block diagram of a subscriber system 118 of tracking system 100. Subscriber system 118 includes non-volatile data storage 302, one or more processing units 304, working memory 306, one or more user I/O devices 308, and a network interface 310, all intercommunicating via a bus 312. Nonvolatile data storage 302 (e.g., hard disk drives, optical disk drives, solid state memory, etc.) stores data and code that is retained therein even when subscriber system 118 is powered down. Working memory 306 stores data and code that, when processed by processing unit(s) 304, imparts functionality to subscriber system 118. User input/output devices 308 (e.g., keyboard, mouse, monitor, etc.) provide a means of interaction between subscriber system 118 and a subscriber of system 100. Network interface 310 provides a communication link between subscriber system 118 and internetwork 122 such that subscriber system 118 can communicate with servers 104(1-n) and other components of tracking system 100 over internetwork 122.

Working memory 306 includes an operating system 314, one or more application programs 316, a subscriber API 318, a subscriber application 320, and an augmented location data presentation module 322. Like in FIG. 2, data and code are shown in working memory 306 as functional blocks for the sake of clear explanation. It should be understood, however, that the various functions of subscriber system 118 need not be run by any particular module of working memory 306 and may be grouped in any manner. The modules in working memory 306 are loaded into working memory 306, such as from non-volatile data storage 302, when subscriber system 118 is powered up.

The programs in working memory 306 provide the following functions. Operating system 314 (e.g., Windows Vista, Palm OS, Windows Mobile, Verizon V CAST, etc.) provides low level control of subscriber system 118 and provides a platform on top of which the other modules can operate. Application programs 316 represent other miscellaneous applications (e.g., security applications, web browsers, etc.) running in working memory 306. Subscriber API 318 (in conjunction with subscriber API 218 of server 104 shown in FIG. 2) facilitates bi-directional communication between the various modules running in working memory 306 (particularly subscriber application 320) and the programs running on servers 104(1-n). Subscriber application 320 provides overall control and management of the interaction between subscriber system 118 and servers 104(1-n). Augmented location data presentation module 322 receives augmented location data from one or more of servers 104(1-n), optionally formats the augmented location data, and then presents the augmented location data to the subscriber via a display device 308.

Subscriber application 320 controls and coordinates the interaction between subscriber system 118 and servers 104(1-n) so that a subscriber can obtain customized augmented location data (and/or sensor data) from tracking device 102. For example, subscriber application 320 provides a graphical user interface so that a subscriber using subscriber system 118 can set up and initialize his tracking account on a server 104. Subscriber application 320 also allows a subscriber to "log in" to a server 104 to use the tracking services provided by the server 104. Subscriber application 320 also allows a subscriber to associate particular tracking devices 102 with the subscriber's account, as well as, allows a subscriber to update his profile in subscriber profile database 106. Furthermore, if a subscriber has multiple tracking devices 102 associated with his account, subscriber application 320 allows a subscriber to indicate which associated tracking device 102 that a server 104 should provide location data for. In addition, subscriber application 320 allows a subscriber to select what augmentation routines 228 to employ (if the augmentation routines are not already selected in the subscriber's profile.

In the present embodiment, subscriber application 320 is an Internet-based client application (e.g., a web page running on subscriber system 118, etc.) that interacts with control and coordination module 224 on a server 104. Thus, control and coordination module 224 (or a program controlled by module 224 on server 104) acts as an internet host to subscriber application 320. In this case, subscriber application 320 is a web-page downloaded to subscriber system 118 from a server 104. Accordingly, control and coordination module 224 (or a host program controlled by module 224) provides the web-page to subscriber system 118, authenticates the subscriber using the subscriber application 320, receives tracking instructions from the subscriber application 320, provides augmented location data to subscriber system 322, and creates or updates profiles in subscriber profile database 106 based on information input by the subscriber through subscriber application 320. Examples of tracking instructions include a subscriber's selection of one or more tracking devices 102 associated with the subscriber's account, the subscriber selecting one or more augmentation routines 228, for example, from a list of augmentation routines provided to subscriber application 320 by control and coordination module 224, and so on. In other cases, subscriber application 320 can be a stand-alone client application running in working memory 306.

Augmented location data presentation module 322 presents augmented location data received by subscriber application 320 to a subscriber using subscriber system 118. In particular, augmented location data presentation module 322 receives augmented location data from subscriber application 320 (communicating with server 104 through subscriber API 318), formats the augmented location data for presentation by subscriber system 118, and then presents the augmented location data to a subscriber via one or more of user I/O device(s) 308, such as a computer monitor or other display.

Because augmented location data presentation module 322 is located on subscriber system 118 rather than on server 104, the augmented location data presentation process is advantageously bifurcated. In particular, server 104 only needs to provide augmented location data in a single format to all subscriber systems 118(1-$p$), and the associated subscriber system 118 can format the location data for presentation on that subscriber system 118, whether it be a computer, a PDA, cellular phone or other device. In addition, such bifurcation also will conserve bandwidth between the server 104 and the subscriber system 118 because the augmented location data sent from the server 104 can be compressed or can be sent in a pre-compiled form.

It should be noted that subscriber API 318, subscriber application 320, and augmented location data presentation module 322 can be downloaded from one of servers 104(1-$n$) and installed on a subscriber system 118 as required. For example, if subscriber system 118 was a cellular telephone, then subscriber API 318, subscriber application 320, and augmented data presentation module 322 could be downloaded from one of servers 104 and installed in subscriber system 118 (optionally for a fee). In this manner, the present invention provides convenient and universal access to its tracking services.

Figure 4:
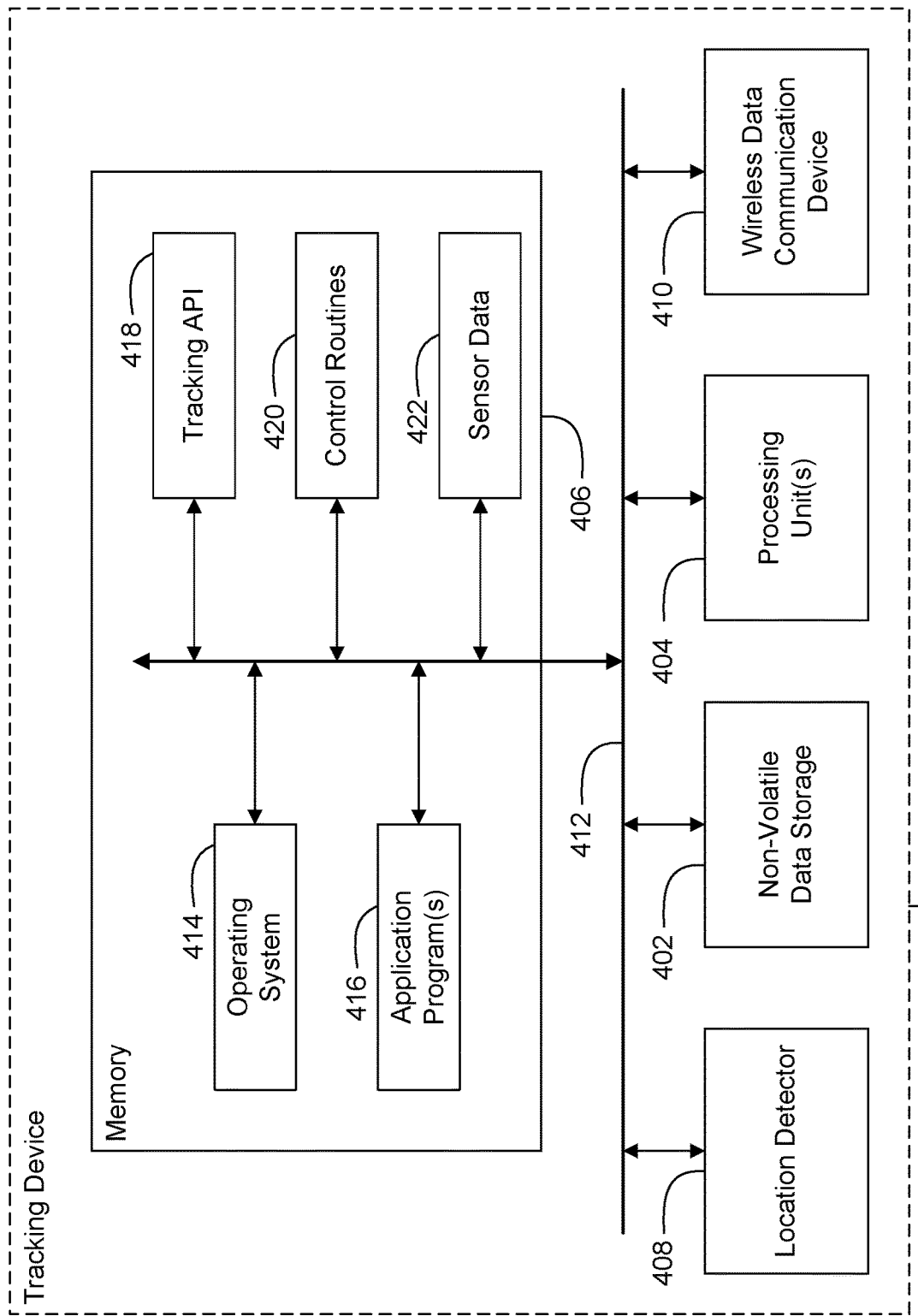
FIG. 4 is a block diagram of a tracking device of the tracking system of FIG. 1.

FIG. 4 is a block diagram of a tracking device 102(1-$m$) of tracking system 100. Tracking device 102 includes nonvolatile data storage 402, one or more processing unit(s) 404, working memory 406, a location detector 408 (e.g., a GPS receiver), and a wireless data communication device 410, all intercommunicating via a bus 412. Nonvolatile data storage 402 (e.g., solid state memory, etc.) stores data and code that is retained therein even when tracking device 102 is powered down. Working memory 406 stores data and code that, when processed by processing unit(s) 404, imparts functionality to tracking device 102. Location detector 408 determines the geographical location of tracking device 102, for example, through a network of satellites, a network of cellular telephone towers, etc. Wireless data communication device 410 provides a communication link to tracking interface 112 such that tracking device 102 can communicate with devices on internal network 114, such as servers 104(1-$n$). In the present embodiment, wireless data communication device 410 is a cellular communications package operative to communicate with tracking interface 112 via a wireless cellular network. Alternatively, wireless data communication device 410 communicates with tracking interface 112 by some other means, including but not limited to, radio, satellite, a wireless WAN (e.g., at "hotspots"), etc. Tracking device 102 can also include one or more sensors (not shown) also communicating on bus 412, such as a temperature sensor, a motion sensor, a battery life sensor, a pressure sensor, etc. as will be further described below.

Working memory 406 includes an operating system 414, one or more application program(s) 416, a tracking API 418, a plurality of control routines 420, and sensor data 422. Operating system 414 provides low level control of tracking device 102 and provides a platform on top of which the other programs can operate. Application programs 416 represent other miscellaneous applications (e.g., security applications, power management applications, etc.) running in working memory 406. Tracking API 418 facilitates bidirectional communication between the various modules of tracking device 102 and tracking interface 112. Because tracking interface 112 communicates over internal network 114, tracking API 418 also facilitates communication between tracking device 102 and the other components (e.g., servers 104(1-$n$)) of system 100 that are connected to internal network 114. Control routines 420 control and coordinate the overall operation of tracking device 102 and enable tracking device 102 to carry out its intended tracking functions. Sensor data 422 stores information detected by other sensors incorporated into tracking device 102. In addition, sensor data 422 can store location data detected by location detector 408. Furthermore, in the present embodiment sensor data 422 contains multiple samples of sensor data that were collected over a predetermined time frame from the various sensors in tracking device 102, including multiple samples of location data.

Control routines 420 enable tracking device 102 to provide location data (and optionally other sensor data) to servers 104(1-$n$) via tracking API 418 and tracking interface 112. For example, one control routine 420, responsive to receiving a location request signal from a server 104 via tracking interface 112, requests location data from location detector 408, receives the location data, and provide that location to the requesting server 104 via tracking API 418 and tracking interface 112. Another control routine 420 is operative to automatically request location data from location detector 408, receive the location data, and provide the location to data to one of servers 104 at predetermined time intervals. Another control routine 420 can store the location data generated by location detector 408 in sensor data 422 at predetermined time intervals and/or when location data is requested by a server 104. Yet another control routine 420 can monitor the location data detected by location detector 408 and generate an alert signal when location detector 408 indicates that the tracking device 102 is inside or outside a predetermined boundary, such as in the case of a geofence described above. Still another control routine 420 can provide an alert signal and/or location data when the location data generated by location detector 408 indicates that the tracking device 102 is within a predetermined proximity to a registered sex offender's address or an adult book store. Because control routines 420 can be tailored to particular geographical areas, servers 104 are operative to update the control routines 420 in tracking devices 102(1-$m$) remotely via tracking interface 112 and tracking API 418.

As the above examples indicate, the scope of operations that control routines 420 can impart to tracking devices 102 is very broad. In addition, a server 104 can customize the control routines 420 in the tracking device 102 as necessary to help carry out particular augmentation routines 228 employed by the server 104. For example, a server 104 may load (or cause to be loaded from non-volatile data storage 202) various control routines 420 in tracking device 406 based on the associated subscriber's profile stored in subscriber profile database 106. In addition, as noted above, control routines can also monitor other sensors incorporated into tracking device 102 and store data acquired from those sensors in sensor data 422 as required. Furthermore, control routines 420 can send alerts to servers 104 (which in turn can send the alerts to subscriber systems 118(1-p)) based on the location data generated by location detector 408 or the sensor data recorded by other sensors. For example, as described above, if one of control routines 420 defined a geofence program, then that control routine 420 could alert one of servers 104 if the location data from location detector 408 indicated that the geofence boundary had been broken. Similarly, a control routine 420 could monitor other sensor data (e.g., a temperature sensor, pressure sensor, etc.) and alert a server 104 if the control routine 420 believes that the tracking device is not being worn correctly, for example, by a child.

Figure 5:
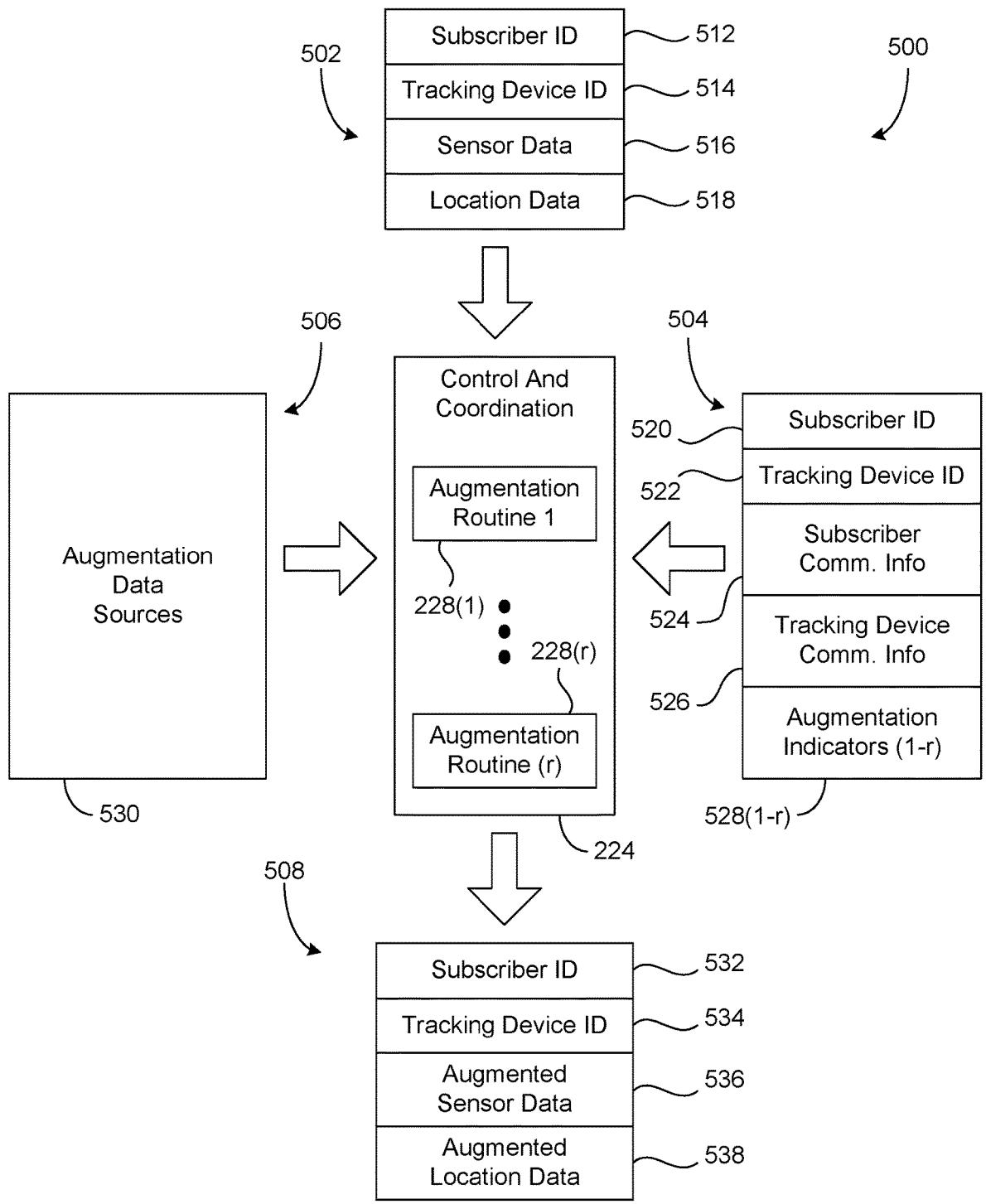
FIG. 5 is a relational diagram 500 showing the data flow within the tracking system shown in FIG. 1.

FIG. 5 is a relational diagram 500 showing data flow within the tracking system 100 of FIG. 1. In diagram 500, control and coordination module 224 of a server 104 receives three data sets 502, 504, and 506 as inputs and provides an augmented data set 508 as an output. Input data set 502 shows an example of data sent by tracking device 102 and includes a subscriber ID 512, a tracking device ID 514, sensor data 516, and location data 518. Input data set 504 shows an example of data stored in a subscriber profile retrieved from subscriber profile database 106 and includes a subscriber ID 520, a tracking device ID 522, subscriber communication information 524, tracking device communication information 526, and one or more augmentation indicator(s) 528(1-r). Input data set 506 includes data from augmentation data sources (e.g., public databases 120, vendor information database 108, etc.) that are used by augmentation routines 228 to augment location data and, optionally, other sensor data.

Referring to input data set 502, subscriber ID 512 includes data uniquely identifying a particular subscriber using one of subscriber systems 118. Similarly, tracking device ID 514 includes data uniquely identifying the tracking device 102 that is transmitting the data contained in input data set 502. The identified tracking device 102 is associated with the subscriber identified by subscriber ID 512. Sensor data 516 includes data recorded by one or more sensors contained in tracking device 102. For example, sensor data 516 might include the output from a temperature sensor, the output of a pressure sensor to determine if the shoe is being worn, the output of a charge sensor to indicate the charge of the tracking device's battery, etc. As yet another example, sensor data 516 might include the output from a motion sensor that indicates if the tracking device 102 has been moved within a prior predetermined amount of time. Finally, location data 518 includes data (e.g., latitude and longitude coordinates, etc.) indicating the geographical location of the tracking device 102. Optionally, sensor data 516 and location data 518 includes more than one sample of sensor and/or location data.

Referring to input data set 504, subscriber ID 520 includes data uniquely identifying a particular subscriber using a subscriber system 118. Subscriber ID 520 includes the same subscriber identifier as subscriber ID 512 in input data set 502. Tracking device ID 522 includes data uniquely identifying one of tracking devices 102(1-m). In the present embodiment, tracking device ID 522 includes the same tracking device identifier as tracking device ID 514 in input data set 502. As stated above, in a particular embodiment, a subscriber 118 can have multiple tracking devices 102 and subscriber profiles, where each of the profiles is associated with a different one of the subscriber's tracking devices 102. Subscriber communication information 524 includes data (e.g., an internet protocol (IP) address, a phone number for sending a text message, a network ID, etc.) that permits a server 104 to communicate augmented location data to the subscriber identified by subscriber ID 520 on the associated subscriber system 118. Tracking device communication information 526 includes data (e.g., a unique network identifier) that enables a server 104 to communicate with the tracking device 102 identified by tracking device IDs 522 and 514. Augmentation indicators 528(1-r) indicate the augmentation routines 228 that control and coordination module 224 will perform on the location data 518 and, optionally, the sensor data 516. Augmentation indicators 528(1-r) can be preset by the subscriber when that subscriber establishes an account with one of servers 104 and sets up his subscriber profile stored in database 106. In addition, augmentation indicators 528 can also be selected by the subscriber directly through subscriber application 320 when the subscriber requests augmented location data. If the subscriber has not set augmentation indicators 528(1-r), then default augmentation indicators 528(1-r) (e.g., augment location with a map, etc.) can be set by a server 104 when establishing the subscriber's account. However, as described above, augmentation indicators 528(1-r) are completely customizable by individual subscribers such that each subscriber receives customized augmented location data.

Note that there are many ways to implement augmentation indicators 528(1-r) for use with the present invention. For example, in one embodiment, augmentation indicators 528(1-r) can include a programmable flag for every augmentation routine 228. A set flag would indicate that a particular augmentation routine 228 was enabled by the subscriber, whereas an unset flag would indicate an augmentation routine 228 that was disabled by the subscriber. Alternatively, each augmentation routine 228 could be identified by a unique identifier, and augmentation indicators 528(1-r) would include only the unique identifiers for the augmentation routines 228 that were enabled by a subscriber. In any case, augmentation indicators 528(1-r) include enough information to indicate to control and coordination module 224 at least those augmentation routines 228 that are enabled by the subscriber 118.

Turning now to input data set 506, input data set 506 includes one or more augmentation data sources 530. Augmentation data sources 530 can be public or private data sources and include input data from any data source that control and coordination module 224 requires to augment location data according to a subscriber's specifications. For example, augmentation data sources may include data from one or more public databases, such as a sex offender registry or a telephone directory. In addition, augmentation data sources 530 can also include private databases, such as vendor information database 108. In a particular embodiment, control and coordination module 224 will retrieve augmentation data from augmentation data sources 530 after it determines which augmentation indicators 528(1-r) are selected in data set 504. Because the augmentation indicators 528(1-r) indicate particular augmentation routines 228, control and coordination module 224 can access the needed augmentation data from data sources 530 based on the specified augmentation routines 228. For example, where the selected augmentation routine 228 augments location data 518 with the address(es) of nearby child predators, control and coordination module 224 would retrieve information from a sex offender registry, but would not necessarily access a telephone directory or vendor information database 108.

Once control and coordination module 224 receives input data from input data sets 502, 504, and 506, control and coordination module 224 calls the augmentation routines 228 selected by augmentation indicators 528(1-r) and augments the location data 518 (and optionally sensor data 516) according to the enabled augmentation routines 228(1-r). Control and coordination module 224 can employ scheduling to run the enabled augmentation routines 228(1-r) in a particular order if some of the data augmentation routines 228 conflict with one another or to use time more efficiently. When all location data augmentation routines 228 are complete, control and coordination module 224 transmits output data set 508 to a subscriber system 118 via internetwork 122 based on subscriber communication information 524.

Augmented output data set 508 includes a subscriber ID 532, a tracking device ID 534, augmented sensor data 536, and augmented location data 538. Subscriber ID 532 includes the same unique subscriber identifier as subscriber ID 512 and subscriber ID 520. Tracking device ID 534 includes the same unique tracking device identifier as tracking device ID 514 and tracking device ID 522. Augmented sensor data 536 includes at least some of sensor data 516 that was augmented by one or more of augmentation routines 228(1-r) that were called by coordination module 224 based on the augmentation indicators 528(1-r). Similarly, augmented location data 538 includes location data 518 that was augmented by one or more of augmentation routines 228(1-r) that were called by control and coordination module 224 based on augmentation indicators 528(1-r). Again, control and coordination module 224 communicates output data set 508 to the associated subscriber 118 by utilizing subscriber communication information 524 contained in data set 504. Once subscriber 118 receives the output data set 508 (via subscriber API 318), augmented location data presentation module 322 formats and presents the augmented location data 528 and augmented sensor data 536 to the subscriber based on the subscriber system 118.

Several examples of the present invention will now be described with respect to FIGS. 1-5 to illustrate the advantages and benefits of the present invention. According to a first example, a subscriber has set an augmentation indicator 528 in his profile to select an average speed and direction augmentation routine 228. When the subscriber requests augmented location data from a server 104 via subscriber application 320 on subscriber system 118, control and coordination module 224 retrieves input data sets 502 and 504 from their respective sources and calls the associated average speed and direction augmentation routine 228. Because the average speed and direction augmentation routine 228 requires several location data samples, control and coordination module 224 tracking s several samples of location data from tracking device 102 if location data 518 does not include several samples of location data. The called augmentation routine 228 then calculates the average speed and direction of the associated tracking device 102 based on the samples of location data 518. Then, control and coordination module 224 forwards output data set 508, including the augmented location data 538 (i.e., average speed and direction) to the subscriber based on the subscriber communication information 524 in the subscriber's subscriber profile.

According to a second example, a subscriber has set an augmentation indicator 528 in his profile to select an augmentation routine 228 that gives him the nearest street address to the tracking device 102. Then, when the subscriber requests augmented location data from a server 104 via subscriber application 320 on subscriber system 118, control and coordination module 224 retrieves input data sets 502 and 504 and calls the address location augmentation routine 228. The address location augmentation routine 228 converts the geographical location data 518 into a street address. Then, control and coordination module 224 forwards output data set 508, including the augmented location data 538 (i.e., the street address of tracking device 102) to the subscriber based on the subscriber communication information 524 in the subscriber's subscriber profile.

According to a third example, a subscriber has set an augmentation indicator 528 in his profile to select an augmentation routine 228 that indicates the location(s) of registered sex offender(s) within a specified distance from the current geographical location of tracking device 102. When the subscriber requests augmented location data from a server 104 via subscriber application 320, control and coordination module 224 retrieves input data sets 502 and 504 and calls the sex offender augmentation routine 228. In this case, augmentation routine 228 causes control and coordination module 224 to query an augmentation data source 530 (i.e., a public sex offender registry database 120) for registered sex offenders within the specified distance from the location specified by location data 518. Augmentation routine 228 then compiles the returned sex offenders from augmentation data source 530, and control and coordination module 224 forwards output data set 508, including the augmented location data 538 (i.e., locations of proximate sex offenders) to the subscriber based on the subscriber communication information 524 in the subscriber's subscriber profile. Note in this case, that the subscriber could input the desired sex offender search radius responsive to a query by control and coordination module 224 (caused by sex offender augmentation routine 228) or the radius could already be included in the subscriber's profile and would form a part of data set 504.

In a fourth example, a subscriber has set an augmentation indicator 528 in his profile to select an augmentation routine 228 that indicates the location(s) of a particular business or type of business (e.g., an arcade, etc.) that are near the location of the subscriber's tracking device 102. When the subscriber requests augmented location data from a server 104, control and coordination module 224 retrieves input data sets 502 and 504 and calls the business locator augmentation routine 228. In this case, business locator augmentation routine causes control and coordination module 224 to query an augmentation data source 530 (i.e., a business directory database 120) for the desired businesses based on the location data associated with the tracking device 102. Business locator augmentation routine 228 then compiles the returned business(es) matching the specified search criteria from augmentation data source 530, and control and coordination module 224 forwards output data set 508, including the augmented location data 538 (i.e., location(s) of the specified business(es)) to the subscriber based on the subscriber communication information 524 in the subscriber's subscriber profile. Like in the previous example, the subscriber could input the desired type of business and search radius responsive to a query by control and coordination module 224 (caused by business locator augmentation routine 228) or the type of business and radius could already be included in the subscriber's profile and would form a part of data set 504.

According to a fifth example, a subscriber has set an augmentation indicator 528 in his profile to select an augmentation routine 228 that renders the location on tracking device 102 (and optionally other points of interest) on a map. When the subscriber requests augmented location data from a server 104, control and coordination module 224 retrieves input data sets 502 and 504 and calls the map augmentation routine 228 based on the augmentation indicators 528. In this case, when the map augmentation routine 228 is executed, the augmentation routine 228 places an indicator on a map at a location corresponding to the geographical location indicated by location data 518. Map augmentation routine 228 can utilize various maps, including a road map, an aerial map, etc. Optionally, map augmentation routine 228 can cause control and coordination module 224 to query one of augmentation data sources 530 to retrieve the desired map. Once map augmentation routine 228 is complete, then control and coordination module 224 forwards output data set 508, including the map augmented location data 538 to the subscriber based on the subscriber communication information 524 in the subscriber's subscriber profile.

As discussed above, the augmentation routines 228 are not limited only to augmenting location data 518. Augmentation routines 228 can also augment sensor data 516 received from tracking device. For example, where the tracking device 102 includes a motion sensor, a subscriber can set an augmentation indicator 528 in his profile to select an augmentation routine 228 that augments sensor data to indicate to the subscriber if the tracking device is in, or has recently been, in motion (i.e., the person being tracked is using it). When the subscriber requests augmented sensor data from a server 104, control and coordination module 224 retrieves input data sets 502 and 504 and calls the motion sensor augmentation routine 228 based on the augmentation indicators 528. In this case, when the motion sensor augmentation routine 228 is executed, the augmentation routine 228 retrieves the sensor data 516, determines if the tracking device 102 is in motion (or recently was in motion) based on the samples of sensor data 516, and generates augmented sensor data 536. Once motion sensor augmentation routine 228 is complete, then control and coordination module 224 forwards output data set 508, including the augmented sensor data 536 to the subscriber based on the subscriber communication information 524 in the subscriber's subscriber profile. In this case, the augmented sensor data 536 could be displayed on the subscriber system 118 as an icon that indicates to the subscriber that the associated tracking device 102 is moving or was recently moving.

Again, it should be reiterated that, although the above examples each discuss only one augmentation routine 228 each, control and coordination module 224 can execute as few or as many augmentation routines 228 as are selected by augmentation indicators 528(1-r).

Additionally, as described above, control and coordination module 224 need not send augmented location data 538 to a subscriber system 118 that is entirely ready to present to a subscriber. For example, control and coordination module 224 may only partially compile the augmented location data 538 for presentation purposes. Then, when a subscriber system 118 receives the augmented location data 538 (and optionally augmented sensor data 536), augmented location data presentation module 322 can format the augmented location data for presentation on the particular subscriber system 118. Bifurcating the augmentation platform (servers 104) from the presentation platform (subscribers 118) advantageously reduces the bandwidth between the servers 104 and the subscribers 118. Furthermore, the bifurcation also permits the servers 104 to run augmentation routines and to provide augmentation data 538 without worrying about formatting the augmented data for specific devices. Rather, the formatting occurs on the subscriber side of tracking system 100.

As described thus far, the present invention provides many advantages. First, servers 104 can utilize many different data sources to augment location data received from tracking devices 102 and customize the augmentation processes to individual subscribers. Indeed, the present invention is highly customizable for individual subscribers 118 because each subscriber can choose to employ different pluralities of augmentation routines 228 for different tracking devices 102. In addition, servers 104 can also integrate new public and private data sources easily into augmentation routines allowing the tracking services provided by servers 104 to be quickly and easily updated and expanded. Also, as described above, the present invention can be employed in various electronic devices such as personal computers, personal data assistants, and cellular telephones.

The methods of the present invention will now be described with respect to FIG. 6. For the sake of clear explanation, these methods are described with reference to particular elements of the previously described embodiments that perform particular functions. However, it should be noted that other elements, whether explicitly described herein or created in view of the present disclosure, could be substituted for those cited without departing from the scope of the present invention. Therefore, it should be understood that the methods of the present invention are not limited to any particular element(s) that perform(s) any particular function(s). Further, some steps of the methods presented need not necessarily occur in the order shown. For example, in some cases two or more method steps may occur simultaneously. These and other variations of the methods disclosed herein will be readily apparent, especially in view of the description of the present invention provided previously herein, and are considered to be within the full scope of the invention.

Figure 6:
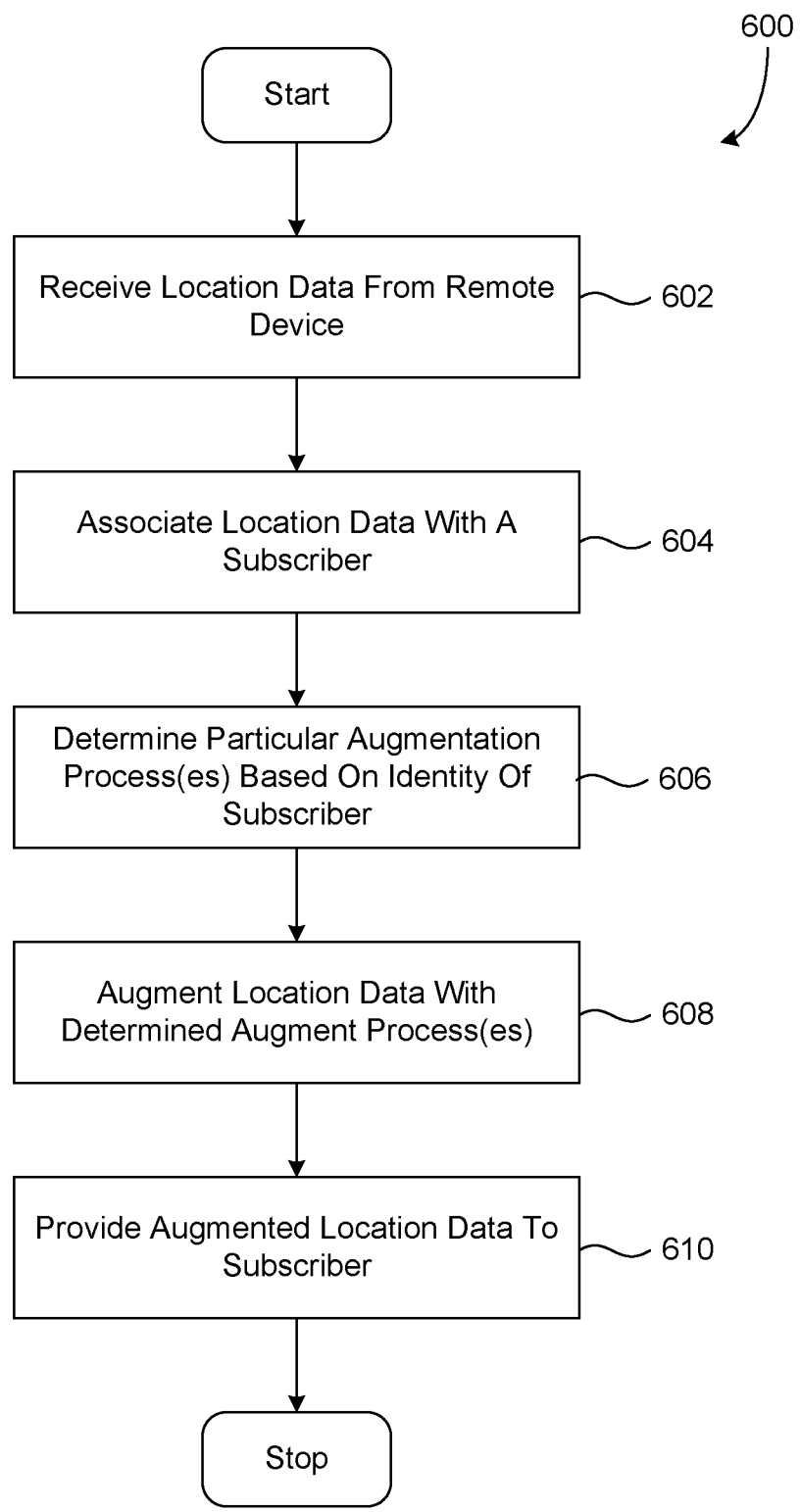
FIG. 6 is a flowchart summarizing one method for providing augmented location data according to the present invention.

FIG. 6 is a block diagram 600 describing a method for providing augmented location data to a subscriber according to the present invention. In a first step 602, a server 104 receives location data from a remote tracking device 102 via tracking interface 112 and internal network 114. Then, in a second step 604, control and coordination module 224 associates the location data with a subscriber by locating a subscriber profile in subscriber profile database 106 associated with the tracking device 102 that sent the location data. Next, in a third step 606, control and coordination module 224 determines the particular augmentation processes 228 to run based on the identity of the subscriber, such as via augmentation indicators 528(1-r). Then, in a fourth step 608, control and coordination module 224 calls the selected augmentation processes 228, and the called augmentation processes 228 augment the location data 518 provided by the remote tracking device 102. Following augmentation, in a fifth step 610, control and coordination module 224 provides the augmented location data to a subscriber 118 associated with the remote tracking device 102.

The description of particular embodiments of the present invention is now complete. Many of the described features may be substituted, altered or omitted without departing from the scope of the invention. For example, alternate augmentation routines (e.g., elevation display augmentations, estimated-time-of-arrival augmentations, etc.), may be added to and/or substituted for those shown herein. As another example, various functions of the tracking system of the present invention can be selectively provided to a subscriber based on that subscriber's subscription level. These and other deviations from the particular embodiments shown will be apparent to those skilled in the art, particularly in view of the foregoing disclosure.

I claim:

1. A method comprising:
receiving, via a wireless network, with a server system, location data from a tracking device, said location data indicative of a location of said tracking device and including information identifying said tracking device;
accessing, with the server system, information associated with said identified tracking device, said information associated with said tracking device identifying one or more databases with types of information selected by a user from among a plurality of types of information;
querying, with the server system, each of said databases to identify instances of the types of information based at least partially on said location data;
augmenting, with the server system, said location data with the instances of the types of information to create augmented location data; and
transmitting, with the server system, said augmented location data to a destination computing device indicated, at least in part, by said information associated with said tracking device, wherein:
the server system and the destination computing device bifurcate augmentation from presentation,
the augmented location data is transmitted in a form that is independent of the destination computing device, and
at least some formatting of the augmented location data for use by the destination computing device is performed by the destination computing device.

2. The method of claim 1, wherein:
querying each of said databased comprises querying a selected set of databases to identify objects based at least in part on said location data includes querying each selected database to identify one or more objects associated with a location within a predefined distance of said location indicated by said location data; and
said step of augmenting said location data includes augmenting said location data to include information indicative of said one or more identified objects.

3. The method of claim 1, wherein said step of querying includes querying at least one public database.

4. The method of claim 1, wherein said step of querying includes querying at least one private database.

5. The method of claim 4, wherein said step of querying includes querying at least one public database.

6. The method of claim 1, further comprising:
establishing electronic communication with said user;
receiving from said user, via said electronic communication, an indication of said user's selection of said types of information;
receiving from said user, via said electronic communication, information associating said user with said tracking device; and
generating said information associated with said tracking device based at least in part on said indication of said user's selection of said selected types of information and said information associating said user with said tracking device.

7. The method of claim 1, further comprising:
receiving location data from a second tracking device, said location data from said second tracking device indicative of a location of said second tracking device and including information identifying said second tracking device;
accessing information associated with said identified second tracking device, said information associated with said second tracking device identifying one or more databases selected by a second user from said plurality of databases, said databases selected by said second user being different from said databases elected by said user;
querying each of said databases selected by said second user to identify objects based at least partially on said location data from said second tracking device;
augmenting said location data from said second tracking device with information associated with said objects identified in said databases selected by said second user to create second selectively augmented location data; and
transmitting said second selectively augmented location data to a destination indicated by said information associated with said second tracking device.

8. The method of claim 1, comprising:
receiving, with the server system, another location of the tracking device;
selecting, with the server system, a plurality of geofences based on proximity between the plurality of geofences and the another location; and
instructing, with the server system, the tracking device to monitor whether subsequent locations of the tracking device traverse any of the plurality of geofences.

9. The method of claim 1, wherein:
the wireless network via which the location data is received is a cellular wireless network;
the destination computing device is different from the tracking device; and
the destination computing device receives the augmented location data via the Internet, without being conveyed via the cellular wireless network.

10. The method of claim 1, wherein receiving the location data comprises receiving a value indicative of a measurement from a sensor worn against person's body, the value being used to form the augmented location data.

11. The method of claim 1, comprising:
steps for augmenting location data.

12. The method of claim 1, wherein:
augmenting the location data comprises obtaining a plurality of locations and determining a speed of the tracking device based on the plurality of locations.

13. The method of claim 1, wherein:
augmenting the location data comprises determining distances between the location and a plurality of places of interest.

14. The method of claim 1, comprising:
selecting a control routine based on the location data or other location data received from the tracking device; and
instructing, via the wireless network, the tracking device to execute the control routine.

15. The method of claim 1, comprising:
transmitting the augmented location data in the same form to another destination computing device that formats the augmented location differently for presentation than how the augmented location data is formatted for presentation on the destination computing device.

16. The method of claim 1, comprising:
receiving temperature and motion sensor data associated with the location from the tracking device, wherein the tracking device comprises a wearable sensor; and
augmenting the location data based on the temperature and motion sensor data.

17. The method of claim 1, comprising:
steps for enabling tracking device to provide location data.

18. The method of claim 1, wherein augmenting the location data comprises:
determining speed and direction of the tracking device; and
using the speed and direction to estimate a time of arrival of the tracking device at a different location.

19. The method of claim 1, comprising:
steps for customizing augmentation routines.

20. The method of claim 1, comprising:
receiving location data from a fleet of vehicles; and
estimating times of arrival for the fleet of vehicles based on the location data received from the fleet of vehicles.

21. A tangible, non-transitory, machine-readable medium storing instructions that, when executed by a computer system, effectuate operations comprising;
receiving, via a wireless network, with a server system, location data from a tracking device, said location data indicative of a location of said tracking device and including information identifying said tracking device;
accessing, with the server system, information associated with said identified tracking device, said information associated with said tracking device identifying one or more databases with types of information selected by a user from among a plurality of types of information;
querying, with the server system, each of said databases to identify instances of the types of information based at least partially on said location data;
augmenting, with the server system, said location data with the instances of the types of information to create augmented location data; and
transmitting, with the server system, said augmented location data to a destination computing device indicated, at least in part, by said information associated with said tracking device, wherein:
the server system and the destination computing device bifurcate augmentation from presentation,
the augmented location data is transmitted in a form that is independent of the destination computing device, and
at least some formatting of the augmented location data for use by the destination computing device is performed by the destination computing device.

\* \* \* \* \*